United States Patent [19]

Fukuda et al.

[11] Patent Number: 5,173,740
[45] Date of Patent: Dec. 22, 1992

[54] LIQUID PARTICLE ANALYZER AND FLOW CELL THEREFOR

[75] Inventors: Masakazu Fukuda; Hiroyuki Nakamoto, both of Kobe; Hidemichi Tohori, Takasagoshi, all of Japan

[73] Assignee: Toa Medical Electronics Co., Ltd., Kobe, Japan

[21] Appl. No.: 733,612

[22] Filed: Jul. 22, 1991

[30] Foreign Application Priority Data

Sep. 28, 1990 [JP] Japan .................. 2-102710[U]

[51] Int. Cl.$^5$ ............................................ G01N 15/14
[52] U.S. Cl. ........................................ 356/246; 356/72
[58] Field of Search ........................... 356/246, 72, 73

[56] References Cited

U.S. PATENT DOCUMENTS 4,790,653 12/1988 North, Jr. ......................... 356/73

Primary Examiner—Vincent P. McGraw
Attorney, Agent, or Firm—Jones, Tullar & Cooper

[57] ABSTRACT

A flow cell for a fluid particle analyzer comprises a narrow measuring liquid path, liquid introducing paths continuous to this measuring liquid path, liquid specimen nozzles disposed so that the front ends may be opposite to each other across the measuring liquid path, and sheath liquid inlets and waste liquid outlets disposed in the liquid introducing paths, respectively.

The particle analyzer is designed to emit light to the liquid specimen flowing as a sheath flow in the measuring liquid path in the flow cell and detect the light from the particles individually. Since two liquid specimen nozzles are disposed opposite to each other, measurements from the liquid specimen discharging from one of the liquid specimen nozzles can take place while preparation of the other liquid specimen takes place, so that the analysis processing time can be notably shortened.

5 Claims, 8 Drawing Sheets

LIQUID PARTICLE ANALYZER AND FLOW CELL THEREFOR

BACKGROUND OF THE INVENTION

The present invention relates to a particle analyzer for detecting particles optically by passing particles of cells, blood corpuscles, or the like in a sheath flow, and a flow cell used therefor.

As the apparatus for analyzing particles in a sample such as cells and blood corpuscles, a so-called sheath flow system is widely known. In this system, by passing a sheath of liquid around the sample discharged from the a sample nozzle, the sample liquid can be reduced to a fine state in the flow cell. By optical measurement, apparent components in the sample can be measured and analyzed. The "sheath flow" refers to a flow covering or surrounding of the suspension of particles with a laminar flow liquid (sheath liquid), in order to arrange particles precisely in a row in the middle part of a minute aperture (a measuring liquid passage) to allow passage.

Hitherto, as a means to enhance the processing capacity of a flow cytometer, the apparatus disclosed in Japanese Laid-open Patent Hei. 2-176562 is known.

Having plural inlets for feeding a sample liquid, this apparatus is intended to lead the sample liquid into the flow cell from different passages, making it unnecessary to clean the sample liquid when changing over.

The prior art in this publication involves the following problems.

(1) Measurement of a sample an be started only after both sample liquids are led into their nozzle parts and prepared. This is because two nozzles are directed in the same way, and while measuring the sample liquid by passing from one nozzle, if it is attempted to introduce the other sample liquid into the other nozzle, this sample liquid may leak out of the nozzle. If leaking out of the nozzle occurs, it may run into the detecting region, which may give rise to a measuring error. Thus, unless the preparation of both sample liquids is complete, measurement cannot be started, and a shortening of the measurement time cannot be expected (in spite of the merit of simultaneous cleaning of both samples, a waiting time occurs if the two sample liquids are not prepared at the same time).

(2) It is difficult to manufacture double-structure nozzles.

(3) If merely two nozzles are provided, the flowing positions of the two sample liquids are different, and special measures would be required to keep the sheath liquids balanced, but moving the nozzles or moving the optical system as disclosed in the publication (to balance the sheath liquids would be practically impossible.

OBJECTS AND SUMMARY OF THE INVENTION

It is therefore a primary object of the invention to provide a particle analyzer in a simple construction capable of shortening the changeover time of the specimens when measuring plural specimens continuously by disposing plural nozzles for discharging sample liquid in a flow cell, and the flow cell to be used therein.

To achieve the above object, the particle analyzer of the invention, in a preferred embodiment thereof, for passing a sheath liquid around a liquid specimen containing particles, emitting light to the finely controlled flows of liquid specimen, and individually detecting the light from the particles, comprises a flow cell containing a narrow measuring liquid path, liquid introducing paths continuous to the measuring liquid path for introducing liquid into the path, liquid specimen nozzles disposed and held in the liquid introducing paths so that the front ends may be opposite to each other across the measuring liquid path, and sheath liquid inlets and waste liquid outlets respectively disposed in the liquid introducing paths.

The flow cell for the particle analyzer of the invention comprises, in a preferred embodiment, a narrow measuring liquid path, liquid introducing paths continuous to the narrow measuring path for introducing liquid to the path, liquid specimen nozzles disposed and held in the liquid introducing paths so that the front ends may be opposite to each other across the measuring liquid path, and sheath liquid inlets and waste liquid outlets disposed at the liquid introducing paths, respectively.

In this flow cell, moreover, outer covers are disposed so as to surround the liquid specimen nozzles individually, and the sheath liquid inlets are disposed at the outer side of the outer covers while the waste liquid outlets at the inner side of the outer covers.

Still more, in the flow cell, electrodes are disposed. For example, in the liquid introducing paths, liquid specimen nozzles are composed of conductive material to be used also as electrodes.

As shown in FIG. 3, by passing a sheath liquid into a first sheath liquid inlet, while discharging a liquid specimen from a first liquid specimen nozzle and discharging these liquids from a second waste liquid outlet, the first liquid specimen is controlled into a fine flow having the sheath liquid as an outer layer at the measuring liquid path hereinafter referred to as the first state). By irradiating this fine flow portion with light, light signals from particles (such as scattered light and fluorescent light) are detected.

Besides, as shown in FIG. 4, by passing a sheath liquid into a second sheath liquid inlet, while discharging a liquid specimen from a second liquid specimen nozzle and discharging these liquids from a first waste liquid outlet, the second liquid specimen is controlled into a fine flow having the sheath liquid as an outer layer at the measuring liquid path (hereinafter referred to as the second state).

During measurement of the first liquid specimen, to prepare for the second liquid specimen, if the second liquid specimen should leak out from the second liquid specimen nozzle, this liquid specimen flows into the second waste liquid outlet, but not into the measuring liquid path.

During measurement of the second liquid specimen, similarly, if the first liquid specimen should leak out from the first liquid specimen nozzle, this liquid specimen will not flow into the measuring liquid path.

In the first state, as shown in FIG. 5, a small flow of sheath liquid may be passed in from the second sheath liquid inlet, and in the second state, as shown in FIG. 6, a small flow of sheath liquid may be passed in from the first sheath liquid inlet (so that an effect close to (2) below may be obtained).

As shown in FIG. 7, in the first state, by further passing a slight amount of sheath liquid into the second sheath liquid inlet, the first liquid specimen flowing through the measuring liquid path is totally introduced into the outer cover as if being wrapped by the sheath liquid, and is discharged from the waste liquid outlet, and will not be left over in the measuring liquid path. Accordingly, when in the second state, a clean sheath liquid free from contamination by the preceding liquid specimen may be passed, and it holds also true in the reverse case.

By using conductive materials for the liquid specimen nozzles, an electric current can be passed between the liquid specimen nozzles from a constant-current source as shown in FIG. 7, and an impedance change occurring between the liquid specimen nozzles when particles pass through the measuring liquid path may be detected by detecting means. Thus, while passing the liquid specimen in the measuring liquid path, the particles may be detected optically and electrically at the same time. A similar effect may be obtained by passing an electric current by using a conductive material for the outer cover.

DETAILED DESCRIPTION OF THE PREFERRED EMBODIMENTS

Figure 1:
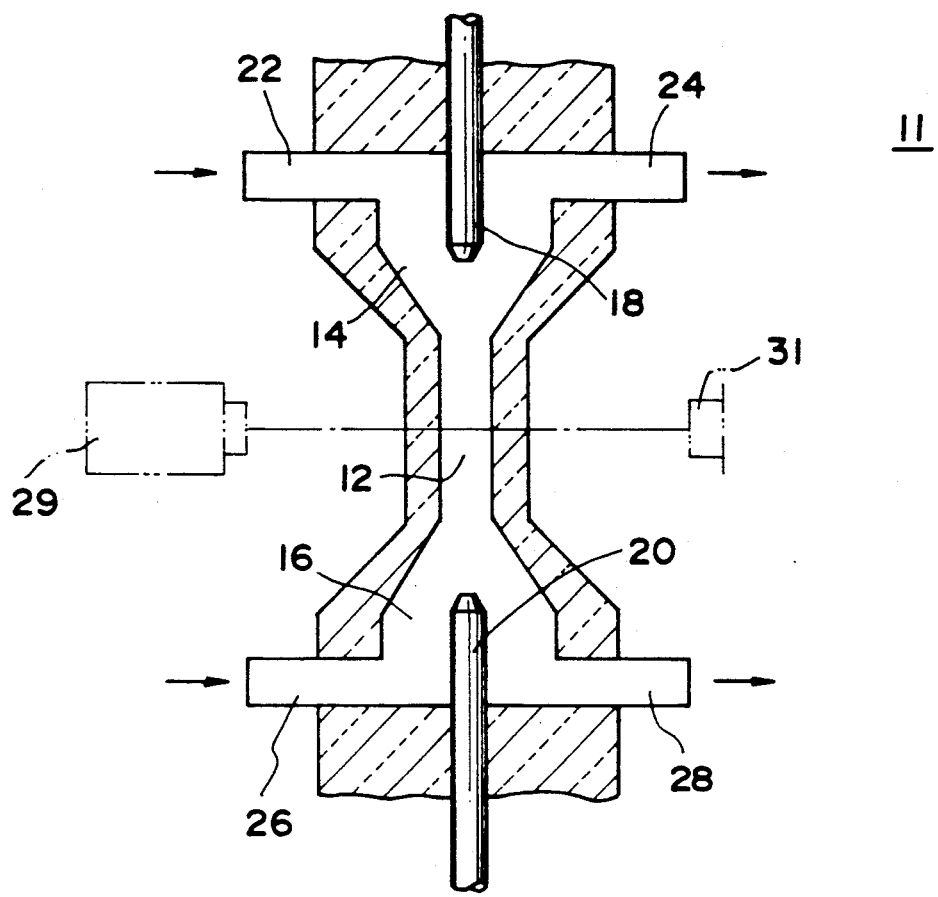
FIG. 1 is a sectional view showing an embodiment of a flow cell for a particle analyzer of the invention.
Figure 2:
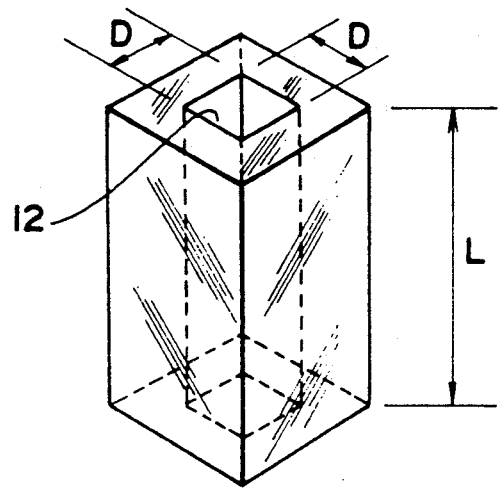
FIG. 2 is a perspective view of a measuring liquid path area in FIG. 1.
Figure 3:
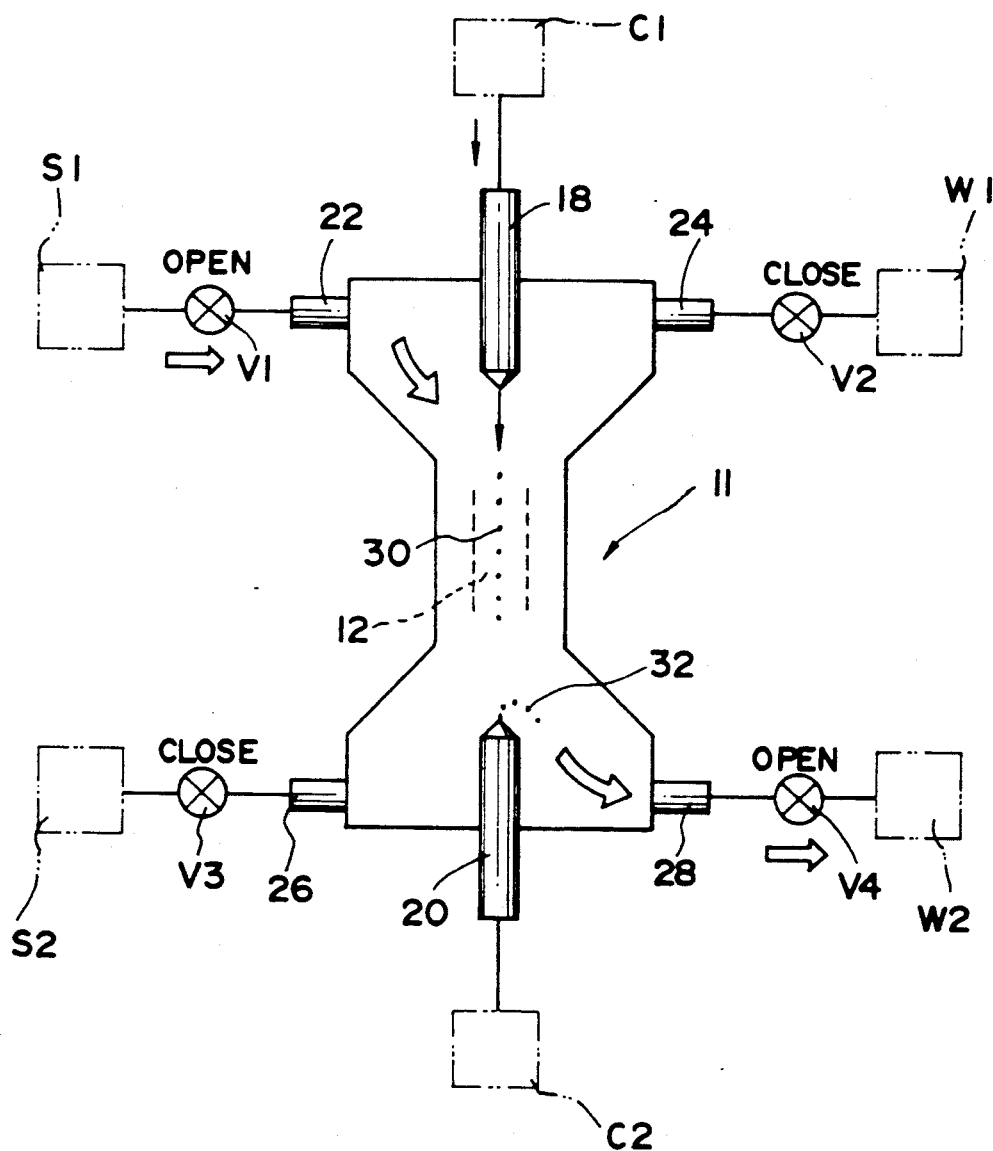
FIG. 3 and FIG. 4 are drawings for explaining the flow of liquid in the flow cell in FIG. 1.
Figure 4:
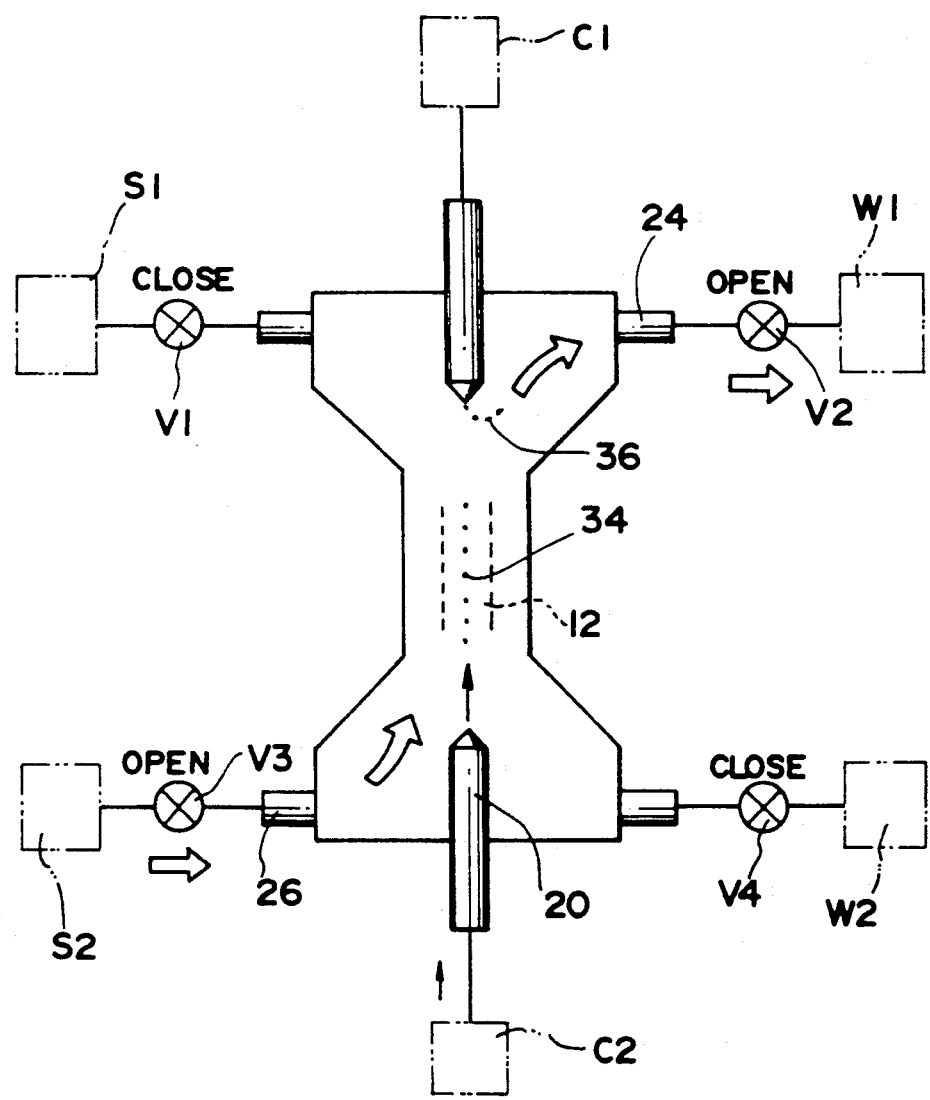
Figure 5:
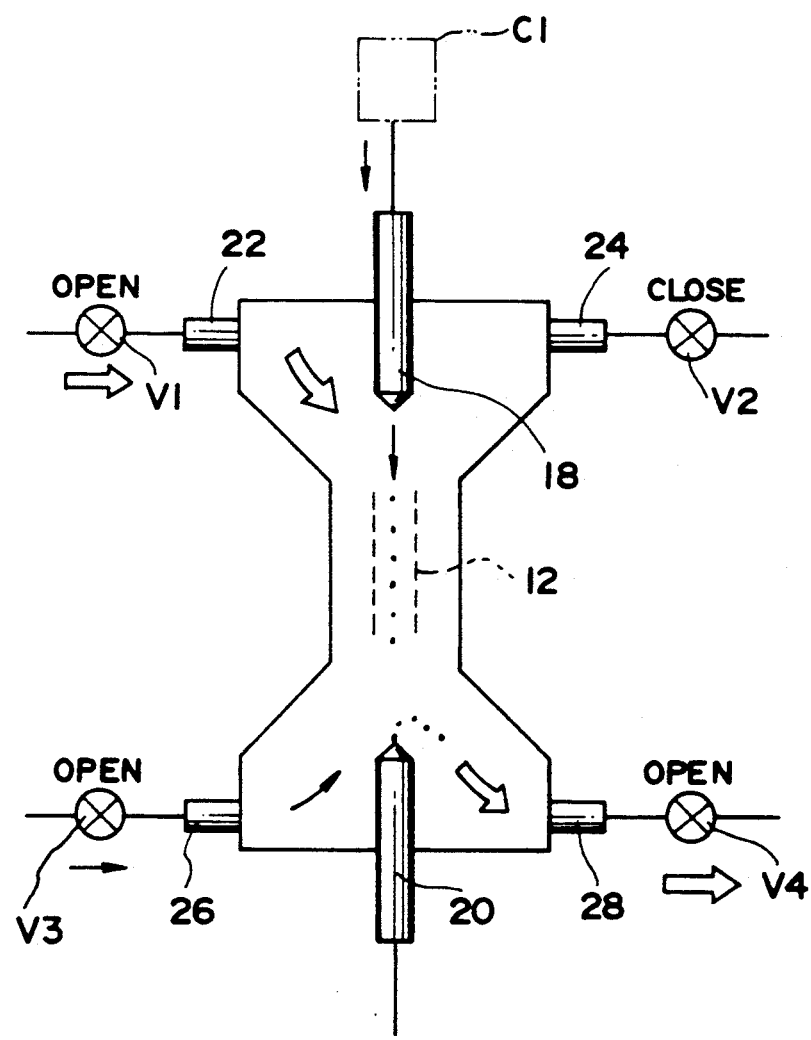
FIG. 5 and FIG. 6 are drawings for explaining other fluid flow.
Figure 6:
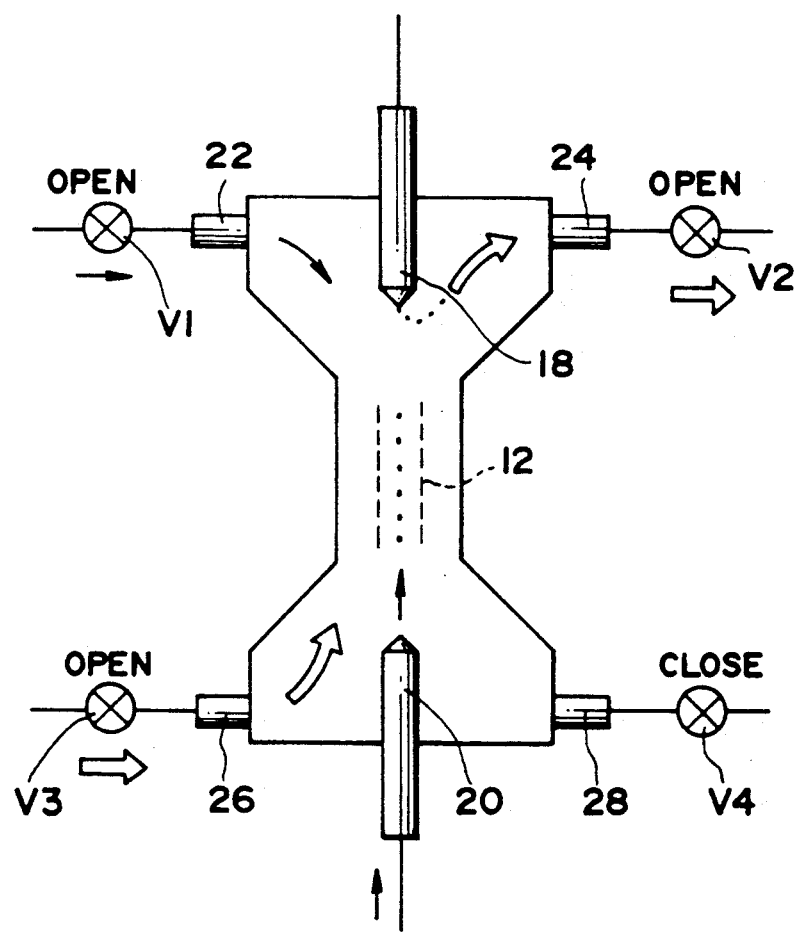

Referring now to the drawings, some of the preferred embodiments of the invention are described in detail below.

Embodiment 1

Figure 8:
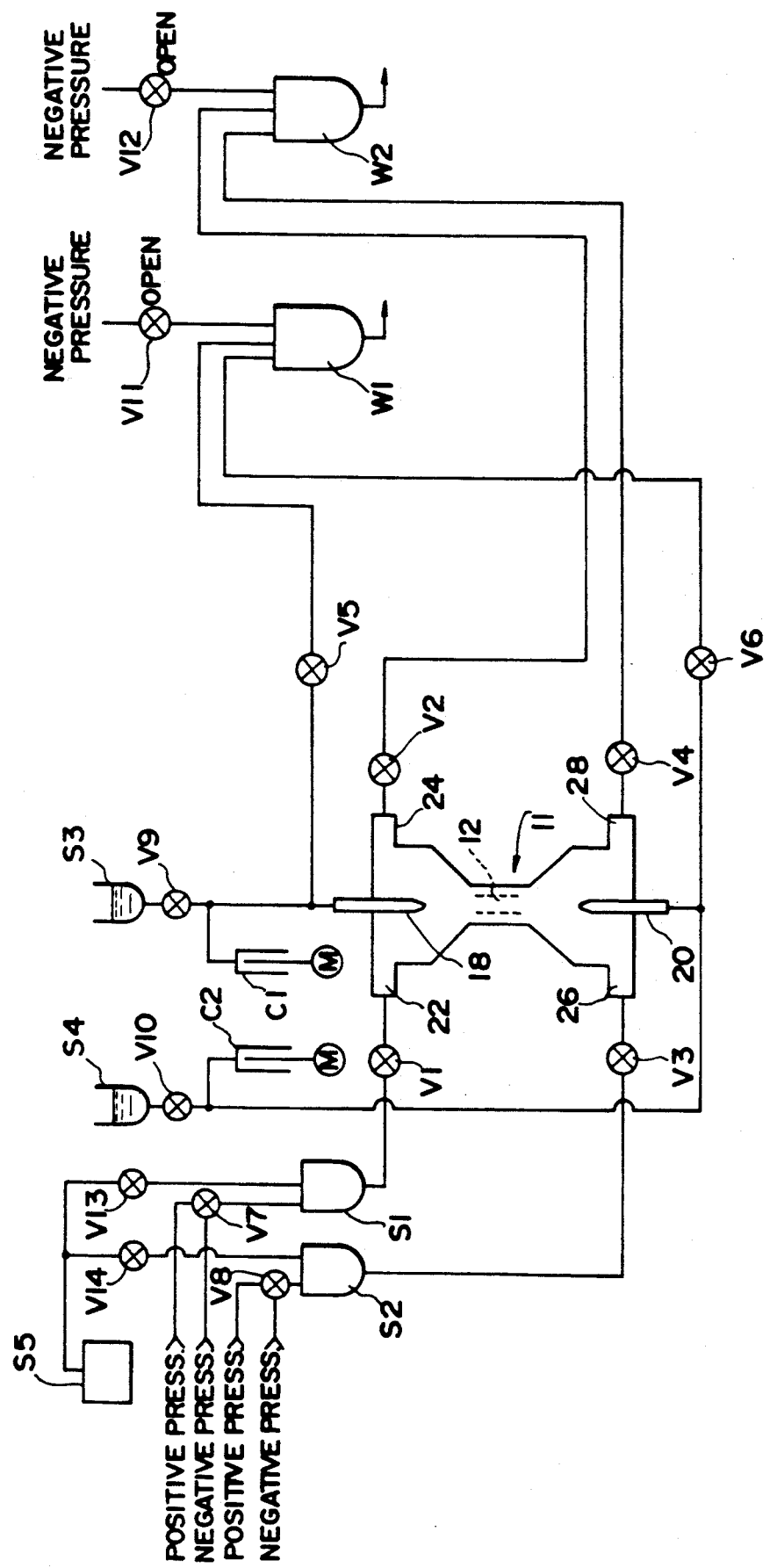
FIG. 8 is a circuit diagram of a particle analyzer using the flow cell shown in FIG. 1 to FIG. 6.

This example relates to a flow cell 10 shown in FIG. 1 to FIG. 6, and a particle analyzer 10 using this flow cell 10. A flow around the flow cell 11 is shown in FIG. 8.

Sheath liquid chambers S1, S2 serve lead in and pool the sheath liquid in the apparatus from a sheath liquid tank S5 disposed outside the analyzer. The sheath liquid chambers S1, S2 are loaded with either positive pressure (a pressure higher than atmospheric pressure) or negative pressure (a pressure lower than atmospheric pressure) through valves V7, V8, respectively, so as to lead in or force out the sheath liquid.

Specimen chambers S3, S4 are intended to temporarily pool the specimen to be analyzed after specific processing such as dilution and dyeing.

Syringes C1, C2 feed their respective liquid specimen into the flow cell 11 at a constant flow rate. Changing over to a valve V11 connected to the negative pressure (vacuum) side, and opening valves V5, V9 for a specified time, the liquid specimen in the specimen chamber S3 is led into the vicinity of the liquid specimen nozzle 18. Thereafter, by closing the valves V5, V9, as the syringe C1 forces out the liquid, the liquid specimen is discharged from the liquid specimen nozzle 18.

By changing to over the valve V7 connected to the positive pressure side and opening valves V1, V4, the sheath liquid is supplied into the flow cell 11, and the waste liquid is discharged.

During measurement of the first specimen, the second liquid specimen in the specimen chamber S4 is similarly led near to the liquid specimen nozzle 20, and is slightly sent out by the syringe C2 and discharged, and the liquid specimen nozzle 20 is filled with the second specimen up to its front end to be ready for the next measurement. At this time, if the liquid specimen leaks out from the liquid specimen nozzle 20, it flows into the waste liquid outlet 28, and will not run into the measuring liquid path 12. When the measurement of the first liquid specimen is over, the second liquid specimen is measured immediately. The flowing area of the first liquid specimen is cleaned by passing a cleaning liquid. By discharging the cleaning liquid from the liquid specimen nozzle 18, the inner wall of the liquid specimen nozzle 18 is cleaned. At this time, too, the liquid from the liquid specimen nozzle 18 will not flow into the measuring liquid path 12. Besides, W1, W2 are waste liquid chambers, 29 is a light emitting element such as a laser source, and 31 is a light receiving element.

The width D of the measuring liquid path 12 (see FIG. 2) is generally 200 to 400 $\mu$m in the case of an optical type alone, or 50 to 150 $\mu$m in the case of electric resistance +optical type, and the length L of the measuring liquid path 12 (see FIG. 2) is generally 2 to 20 mm in the case of an optical type alone, and 50 to 150 $\mu$m in the case of electric resistance +optical type.

Embodiment 2

Figure 7:
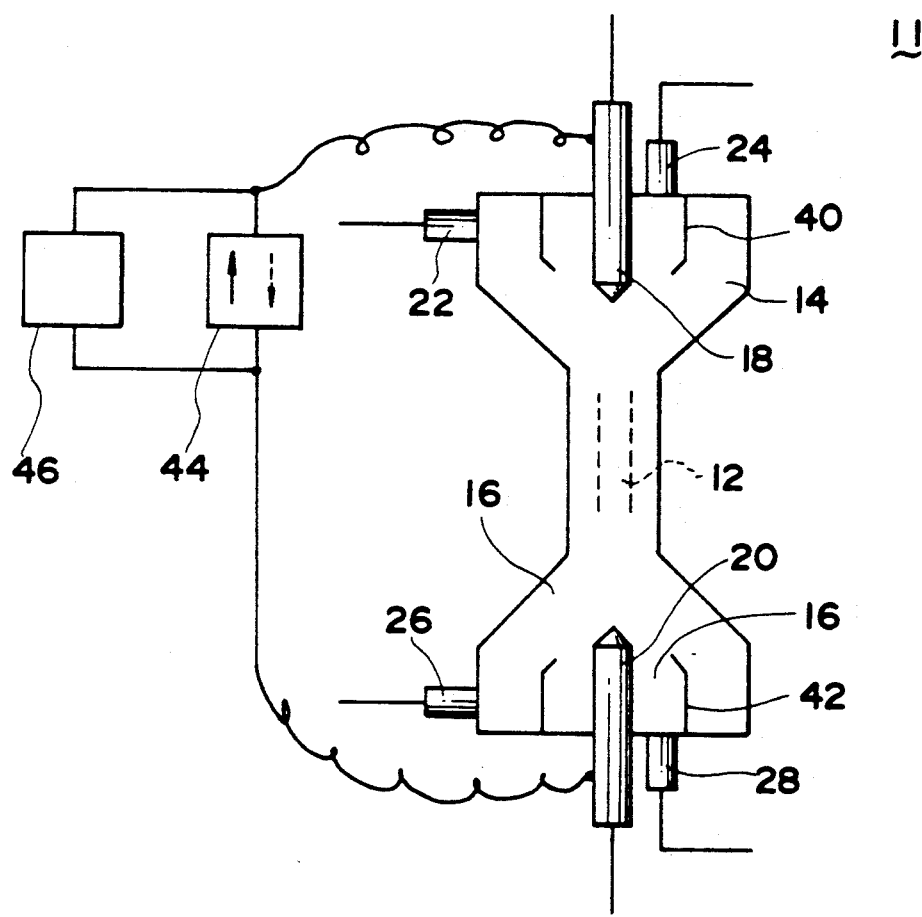
FIG. 7 illustrates another embodiment of a flow cell for a particle analyzer of the invention.
Figure 9:
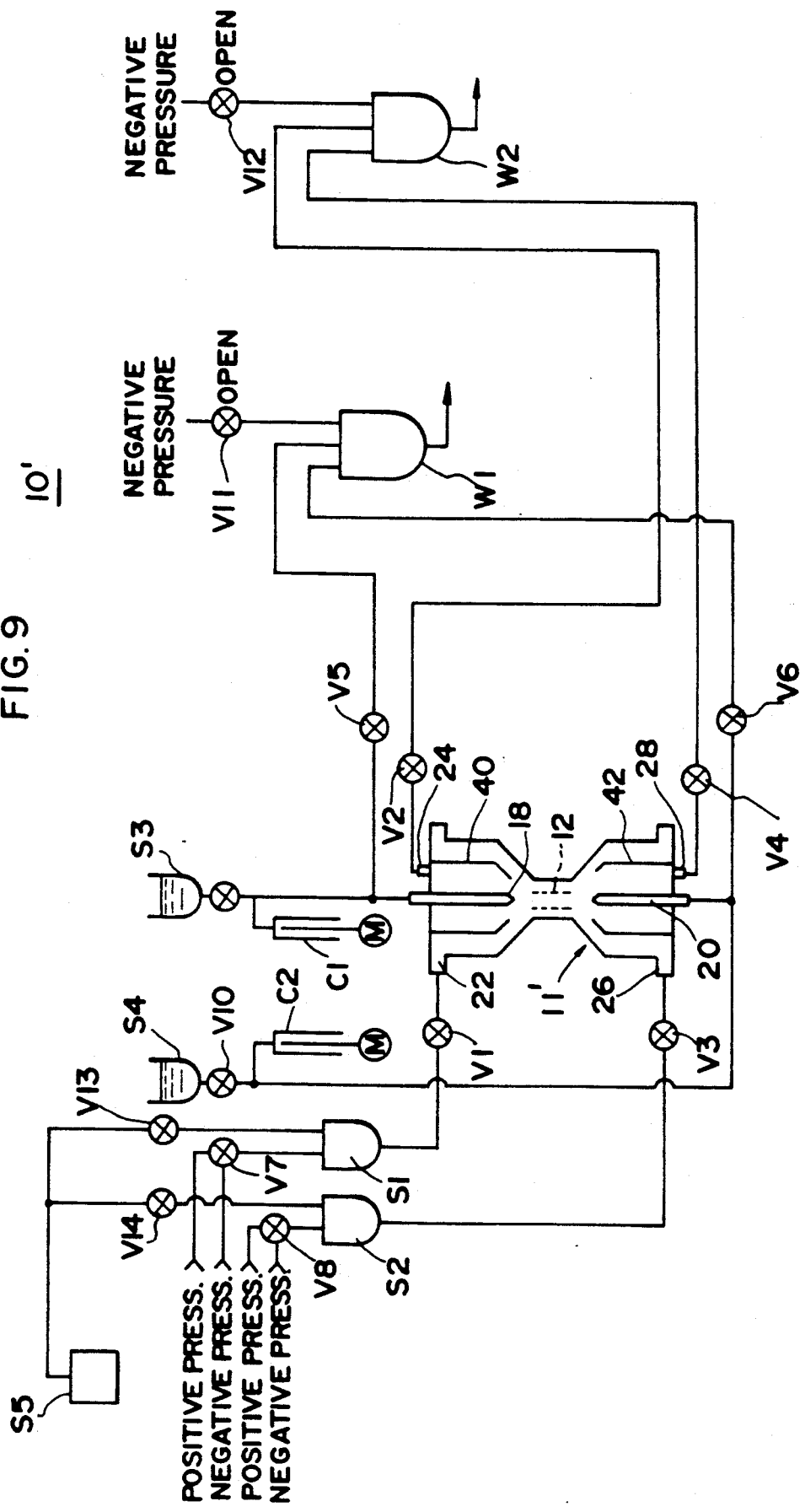
FIG. 9 is a circuit diagram of a particle analyzer using the flow cell shown in FIG. 7.

This example relates to a flow cell 11' shown in FIG. 7 and a particle analyzer 10' using the flow cell, and a flow around the flow cell is shown in FIG. 9.

As shown in FIG. 7, liquid specimen nozzles 18, 20 are made of corrosion-resistant conductive material, and are connected to a constant-current source 44 with wires. In the first state (the state of discharging liquid specimen from the liquid specimen nozzle 18), a constant current is passed so that the liquid specimen nozzle 18 may be positive and the liquid specimen nozzle 20 may be negative. It is intended so that the air bubbles generated at the negative electrode by electrolysis may not flow into the measuring liquid path 12.

In the second state, an the contrary, a constant current is passed so that the liquid specimen nozzle 18 may be negative and the liquid specimen nozzle 20 may be positive. Thus, by alternately changing the current direction in synchronism with the motion of the liquid, generation of air bubbles or electrode corrosion may be suppressed. Also, by the detecting means 46, the signal polarity is changed over so as to detect the signal for only one electrode, for example, the negative electrode.

Meanwhile, instead of using the liquid specimen nozzles also as the electrodes, electrodes may be separately installed in the liquid introducing paths 14, 16. For example, moreover, outer covers 40, 42 may be used as the electrodes.

In FIG. 9, the measuring method is the same as that of Embodiment 1. In Embodiment 1, however, if a contaminated portion of the preceding specimen is left over in the flow cell, or the specimen pops out into the cell from the front ends of the liquid specimen nozzles 18, 20, the cell may be contaminated. Or, when measuring the specimen using resistance by applying positive voltage and negative voltage to the liquid specimen nozzles 18, 20, particles may fly back due to spreading after reducing, which may adversely affect the counting.

In Embodiment 2, it is intended to avoid such effects by using a double tube structure covering the outside of the liquid specimen nozzles 18, 20 with outer covers 40, 42.

While measurements are taken by passing specimen from the liquid specimen nozzle 18 side into the liquid specimen nozzle 20 side, a weak sheath pressure is applied from the sheath liquid inlet 26 side to the outside of the outer cover 42 of the liquid specimen nozzle 20 side, and the waste liquid is recovered from the waste liquid outlet 28 of the inside of the outer cover 42. This is, so to speak, the back sheath system.

Then, passing a liquid specimen from the liquid specimen nozzle 20 side into the liquid specimen nozzle 18 side, it is measured. At this time, a clean sheath liquid is always flowing, while a back sheath liquid is flowing in the spreading part right after reducing, so that particles will not fly back, but run into the outer cover 40.

This invention, arranged as mentioned herein, therefore brings about the following effects.

(1) Two liquid specimen nozzles are made to confront each other and while measuring by discharging a liquid specimen from one liquid specimen nozzle, the other liquid specimen may be prepared in the other liquid specimen nozzle, so that the analysis processing time may be notably shortened.

(2) When outer covers are disposed, the liquid specimen is completely discharged to the outside of the flow cell and is not left over, and the flow cell is not contaminated if used for a long time.

(3) When liquid specimen nozzles or outer covers are used as electrodes, not only optical detection but also electrical detection may be done simultaneously, and analysis of a higher precision is realized.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. In a liquid particle analyzer for passing a sheath liquid around a liquid specimen containing particles, means for emitting light at finely controlled flows of liquid specimen, and individually detecting the light from the particles, and a flow cell, said flow all comprising:

means defining a narrow measuring liquid path;
   means defining liquid introducing paths continuous to the measuring liquid path for introducing liquid into the measuring liquid path;
   liquid specimen nozzles having nozzle outlets, said liquid specimen nozzles being disposed and held in the liquid introducing paths so that the nozzle outlets are opposite to each other across the measuring liquid path; and
   sheath liquid inlets and waste liquid outlets respectively disposed in the liquid introducing paths.

2. A flow cell for a liquid particle analyzer comprising:

means defining a narrow measuring liquid path;
   means defining liquid introducing paths continuous to the measuring liquid path for introducing liquid into the measuring liquid path;
   liquid specimen nozzles having nozzle outlets, said liquid specimen nozzles being disposed and held in the liquid introducing paths so that the nozzle outlets are opposite to each other across the measuring liquid path; and
   sheath liquid inlets and waste liquid outlets respectively disposed in the liquid introducing paths.

3. A flow cell for a liquid particle analyzer as set forth in claim 2, further comprising outer covers disposed so as to surround the liquid specimen nozzles, wherein the sheath liquid inlets are disposed at the outside of the outer covers, and waste liquid outlets at the inside of the outer covers.

4. A flow cell for a liquid particle analyzer as set forth in claim 3, wherein the liquid specimen nozzles are made of conductive material.

5. A flow cell for a liquid particle analyzer as set forth in claim 3 wherein the outer covers are made of conductive material.

* * * * *